United States Patent [19]

Gelbein

[11] 4,327,219
[45] Apr. 27, 1982

[54] NICOTINAMIDE PRODUCTION

[75] Inventor: Abraham P. Gelbein, Plainfield, N.J.

[73] Assignee: The Lummus Company, Bloomfield, N.J.

[21] Appl. No.: 141,943

[22] Filed: Apr. 21, 1980

[51] Int. Cl.³ .......................................... C07D 213/56
[52] U.S. Cl. .................................................. 546/317
[58] Field of Search ....................................... 546/317

[56] References Cited

U.S. PATENT DOCUMENTS 4,008,241 2/1977 Gelbein et al. ...................... 546/317
4,139,536 2/1979 Beschke et al. ..................... 546/317

Primary Examiner—Alan L. Rotman

Attorney, Agent, or Firm—Louis E. Marn; Elliot M. Olstein

[57] ABSTRACT

In the hydrolysis of nicontinonitrile to nicotinamide, the hydrolysis effluent, containing nicotinamide, unconverted nicotinonitrile, ammonia and some ammonium nicotinate is stripped with gaseous ammonia to produce a molten nicontinamide bottoms, essentially free of nicotinonitrile, containing less than 10 wt % water and an overhead containing water vapor, ammonia and nicotinonitrile. An aqueous solution of ammonia and unreacted nicotinonitrile is recovered from the overhead and recycled to the hydrolysis, with gaseous ammonia in the overhead being recycled to the stripping.

10 Claims, 1 Drawing Figure

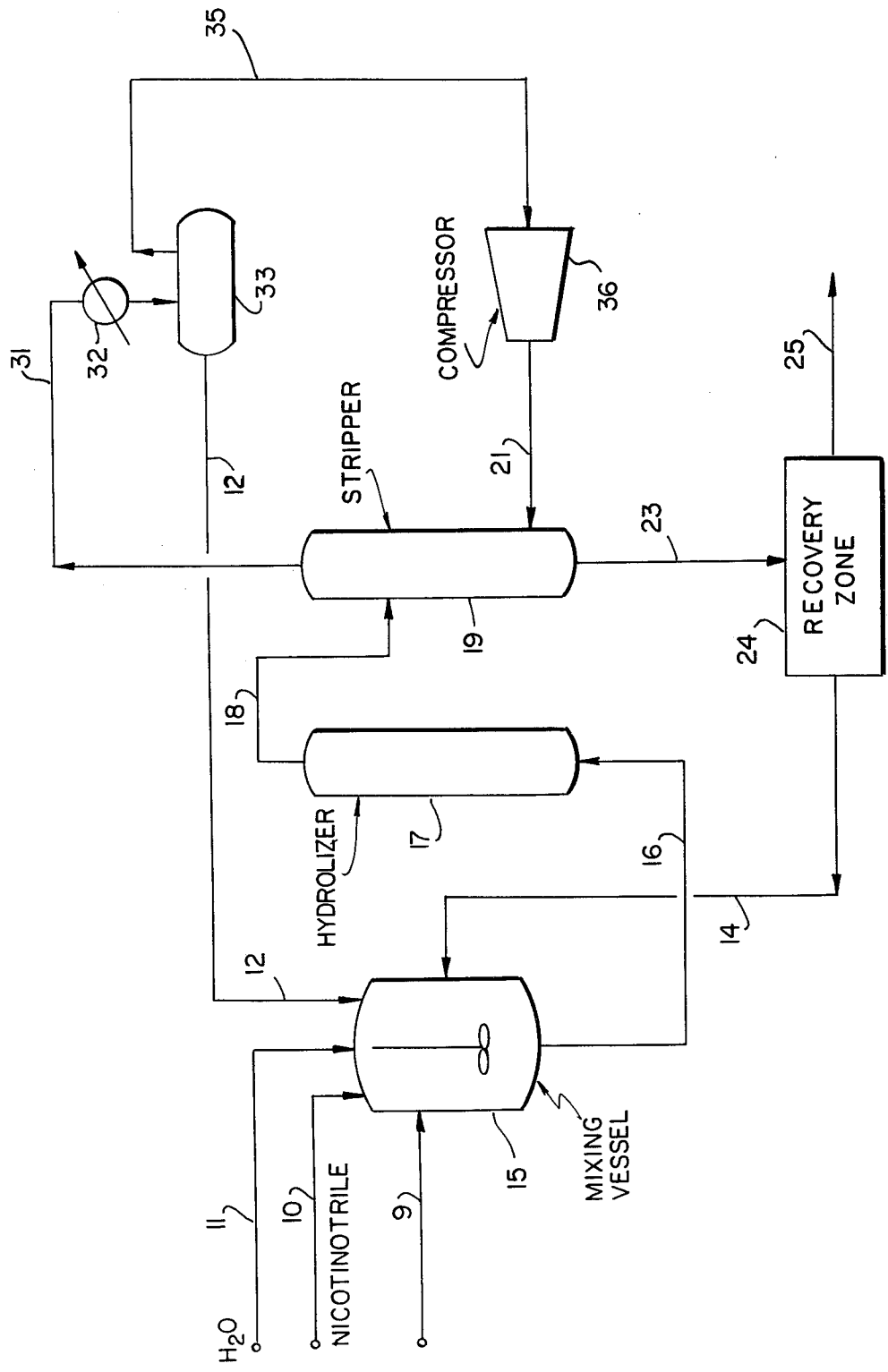

NICOTINAMIDE PRODUCTION

This invention relates to the production of nicotinamide, and more particularly to a new and improved process for producing nicotinamide from nicotinonitrile.

U.S. Pat. No. 4,008,241 discloses a process for hydrolizing nicotinonitrile to nicotinamide with an aqueous ammonia solution. In accordance with the process of such patent, the hydrolysis effluent is introduced into a steam stripping zone to recover an aqueous solution of nicotinamide, and produce an overhead containing water vapor, ammonia and nicotinonitrile, with the overhead product being subsequently distilled to recover aqueous nicotinonitrile for recycle to the hydrolysis.

U.S. Pat. No. 4,139,536 discloses a process for recovering nicotinamide from a nicotinonitrile hydrolysis effluent wherein water is separated at a temperature above the melting point of nicotinamide. The patent discloses the use of falling film evaporators for such recovery.

The present invention is directed to an improvement in a process for hydrolyzing nicotinonitrile to nicotinamide, which includes improved separation of nicotinamide and unreacted nicotinonitrile.

In accordance with the present invention, the effluent produced in the aqueous ammonia hydrolysis of nicotinonitrile to nicotinamide, which contains nicotinamide, unconverted nicotinonitrile, ammonia, ammonium nicotinate and water is stripped with gaseous ammonia to produce a molten nicotinamide bottoms, essentially free of nicotinonitrile, which contains less than 10 wt% water, and an overhead containing water vapor, ammonia and nicotinonitrile. An aqueous solution of ammonia and unreacted nicotinonitrile is condensed from such overhead and recycled to the hydrolysis.

The use of ammonia, as a stripping gas, for the separation and recovery of nicotinamide from the hydrolysis effluent is an improvement over the process as disclosed in U.S. Pat. No. 4,008,241 in that it permits direct recovery of an aqueous nicotinonitrile recycle stream from the stripping operation, without requiring an additional distillation procedure to provide for concentration of the recycle. Moreover, the nicotinamide, recovered as a bottoms product from the stripping, contains lower amounts of ammonium nicotinate as a result of the use of ammonia as a stripping gas.

The ammonia stripping of the hydrolysis effluent is effected to provide a molten nicotinamide bottoms, essentially free of nicotinonitrile, which has a water content of less than 10 wt.%, and preferably less than 1 wt.%. In general, such stripping is effected at a bottoms temperature in the order of from about 270° F. to about 350° F., preferably from about 300° F. to about 330° F., at a pressure from about 0 psig to about 110 psig, and preferably from about 0 psig to about 50 psig. The ammonia is introduced into the bottom of the stripping column in an amount effective to provide the required stripping. In general, the bottoms contains less than 10%, by weight, of ammonium nicotinate, and more generally less than 5%, by weight, of ammonium nicotinate.

The overhead recovered from the stripping is cooled to effect condensation of water containing nicotinonitrile and ammonium. In general, the condensed portion of the overhead has a nicotinonitrile concentration of at least 10% and most preferably at least 20%, with the nicotinonitrile concentration generally being no greater than 60% and most generally no greater than 45% all by weight. Such condensate can be recycled, without further treatment, to the hydrolysis step.

The uncondensed portion of the overhead, which is essentially ammonia, may then be recycled to the stripping operation, as the stripping gas.

The hydrolysis of nicotinonitrile to nicotinamide is effected as generally described in U.S. Pat. No. 4,008,241, which is hereby incorporated by reference. In accordance with such patent, such hydrolysis is generally effected at a temperature from 90° to 150° C., preferably from 100° to 125° C., at a time of from 4 to 8 hours, with the ammonia concentration generally being at least 3 molar, preferably at least 6 molar and generally no greater than 8 molar, preferably no greater than 7 molar. The nitrile conversion is controlled to at least 30%, and preferably at least 40%, and no greater than 70%, and preferably no greater than 60%. The nitrile conversion is controlled by coordinating the ammonia concentration with time and temperature of hydrolysis. As disclosed in such patent, the hydrolysis is preferably effected in the presence of ammonium nicotinate in order to produce nicotinamide at an essentially 100% nicotinamide selectivity. The hydrolysis is generally effected with a nicotinonitrile concentration, expressed as weight product amide per 100 parts of water, of at least 100 parts, and no greater than 300 parts.

The invention will be further described with respect to an embodiment thereof illustrated in the accompanying drawing, wherein:

The drawing is a simplified schematic flow diagram of an embodiment of the present invention for producing nicotinamide.

It is to be understood, however, that the scope of the present invention is not to be limited to the illustrative embodiment.

Referring now to the drawing, fresh feed ammonia in line 9, fresh feed nicotinonitrile in line 10, fresh feed water in line 11, a recycle stream in line 12, comprised of nicotinonitrile, water and ammonia and a recycle stream in line 14, obtained from the nicotinamide recovery operation, are introduced into a mixing vessel, schematically generally indicated as 15. The mixture is withdrawn from vessel 15 through line 16 and introduced as feed to a hydrolysis vessel, schematically generally indicated as 17, in which nicotinonitrile is hydrolyzed to nicotinamide.

The hydrolysis which is effected in vessel 17 is effected at the conditions hereinabove described, and as described in more detail in U.S. Pat. No. 4,008,241.

A hydrolysis effluent, containing nicotinamide, water, ammonia, unreacted nicotinonitrile and ammonium nicotinate is withdrawn from hydrolyzer 17 through line 18 and introduced into the upper portion of a stripping column, schematically generally indicated as 19.

The stripping column is provided with ammonia stripping gas in the lower portion thereof, through line 21, and the column is operated as hereinabove described to recover a molten nicotinamide bottoms, containing less than 10 wt% of water, and which is essentially free of nicotinonitrile. The heating requirements for stripping column 21 can be provided by superheating the ammonia stripping gas and/or indirect heat exchange. As a result of the use of the ammonia stripping gas, there is no necessity for the introduction of steam into the stripping column 19.

A nicotinamide bottoms is withdrawn from stripping column 19 through line 23 and introduced into a nicotinamide recovery zone, schematically generally indicated as 24. The recovery of nicotinamide in recovery zone 24 may be effected by procedures generally known in the art. Thus, for example, as described in U.S. Pat. No. 4,008,241 nicotinamide may be recovered by a crystallization procedure. Nicotinamide product is recovered through line 25, and an aqueous recycle stream, containing ammonium nicotate recovery zone 24 is recycled to the hydrolysis through line 14.

Referring back to the stripping column 19, an overhead, containing ammonia, unreacted nicotinonitrile and water vapor is recovered from column 19 through line 31 and passed through a cooler, schematically generally indicated as 32 in order to condense water containing unreacted nicotinonitrile and ammonia, with a mixed vapor/liquid stream being introduced into a vapor/liquid separator, schematically generally indicated as 33.

Gaseous ammonia withdrawn from separator 33 through line 35 is compressed by compressor 36 and introduced into the stripping column 19, as a stripping gas, through line 21, as hereinabove described.

A recycle stream of water, unreacted nicotinonitrile and ammonia is recovered from separator 33 through line 12 for ultimate recycle to the hydrolysis reactor 17. As a result of the use of ammonia stripping gas in column 19, such recycle stream is recovered with a sufficient nicotinonitrile concentration, without the necessity of employing an additional concentration step in order to provide such a required concentration. Thus, the nicotinonitrile recycle stream is recovered by cooling and partial condensation of the overhead recovered from the stripping column 19.

Numerous modifications and variations of the present invention are possible in light of the above teachings and, therefore, within the scope of the appended claims, the invention may be practiced otherwise than as particularly described.

I claim:

1. In a process for hydrolyzing nicotinonitrile to nicotinamide with an aqueous ammonia solution to produce an aqueous effluent containing nicotinamide, unconverted nicotinonitrile, ammonia and ammonium nicotinate, the improvement comprising:
   stripping the effluent with gaseous ammonia to produce a molten nicotinamide bottoms, essentially free of nicotinonitrile, and containing less than 10 wt.% water, and an overhead containing water vapor, ammonia and nicotinonitrile; condensing from the overhead an aqueous solution of ammonia and unreacted nicotinonitrile; and recycling the said aqueous solution of ammonia and unreacted nicotinonitrile to the hydrolyzing.

2. The process of claim 1 wherein the aqueous solution condensed from the overhead has a nicotinonitrile concentration of at least 10 weight percent and no greater than 60 weight percent.

3. The process of claim 2 wherein the aqueous solution condensed from the overhead has a nicotinonitrile concentration of at least 20 weight percent.

4. The process of claim 3 wherein the molten nicotinamide bottoms contains less than 10 weight percent ammonium nicotinate.

5. The process of claim 4 wherein the stripping is conducted at a bottoms temperature of from 270° F. to 350° F. and a bottoms pressure of from 0 to 110 psig.

6. The process of claim 5 wherein the molten nicotinamide bottoms contains less than 1 weight percent water.

7. The process of claim 5 wherein uncondensed overhead is recycled as stripping gas.

8. The process of claim 2 wherein uncondensed overhead is recycled as stripping gas and the aqueous solution condensed from the overhead is recycled to the hydrolyzing of nicotinonitrile.

9. The process of claim 8 wherein the aqueous solution condensed from the overhead has a nicotinonitrile concentration of at least 20 weight percent.

10. The process of claim 9 wherein the stripping is conducted at a bottoms temperature of from 270° F. to 350° F. and a bottoms pressure of from 0 to 110 psig.

* * * * *